(12) United States Patent
LeVaughn et al.

(10) Patent No.: US 6,197,040 B1
(45) Date of Patent: *Mar. 6, 2001

(54) LANCING DEVICE HAVING A RELEASABLE CONNECTOR

(75) Inventors: Richard Wayne LeVaughn, McDonough, GA (US); John M. Purlee, San Jose, CA (US); Christopher John Ruf, Atlanta; William C. Taylor, Rex, both of GA (US)

(73) Assignee: Lifescan, Inc., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/255,830

(22) Filed: Feb. 23, 1999

(51) Int. Cl.[7] .................................................. A61B 17/32
(52) U.S. Cl. ........................................... 606/182; 128/770
(58) Field of Search ..................................... 606/181, 182, 606/185, 167; 128/770; 604/192–198

(56) References Cited

U.S. PATENT DOCUMENTS

| | | | |
|---|---|---|---|
| 4,503,856 | 3/1985 | Cornell et al. ........................ | 128/314 |
| 4,527,561 | 7/1985 | Burns .................................... | 128/314 |
| 4,535,769 | 8/1985 | Burns .................................... | 128/314 |
| 4,553,541 | 11/1985 | Burns .................................... | 128/314 |
| 4,735,203 * | 4/1988 | Ryder et al. .......................... | 128/314 |
| 4,892,097 * | 1/1990 | Ranalletta et al. ................... | 606/182 |
| 4,895,147 | 1/1990 | Bodicky et al. ...................... | 606/182 |
| 4,976,724 | 12/1990 | Nieto et al. ........................... | 606/182 |
| 5,318,584 | 6/1994 | Lange et al. .......................... | 606/182 |
| 5,350,392 * | 9/1994 | Purcell et al. ........................ | 606/182 |
| 5,356,420 * | 10/1994 | Czernecki et al. ................... | 606/182 |
| 5,423,847 * | 6/1995 | Strong et al. ......................... | 606/182 |
| 5,487,748 * | 1/1996 | Marshall et al. ..................... | 606/182 |
| 5,628,764 * | 5/1997 | Schraga ................................ | 606/182 |
| 5,741,288 * | 4/1998 | Rife ...................................... | 606/181 |
| 5,871,494 * | 2/1999 | Simons et al. ....................... | 606/181 |
| 6,045,567 * | 4/2000 | Taylor et al. ......................... | 606/181 |

* cited by examiner

Primary Examiner—Michael Buiz
Assistant Examiner—Jonathan D. Goldberg
(74) Attorney, Agent, or Firm—James Riesenfeld (57) ABSTRACT

A lancing device has a spring-loaded lancet holder slidably mounted within a housing for carrying a disposable lancet and needle. A slider mounted in a slot in the housing is moved back for cocking the device and, after the lancet is fired, is moved forward to eject the used lancet. A releasable connector reversibly immobilizes the holder while the lancet is being ejected. The releasable connector permits a shortened ejection stroke, which, in turn, permits a shorter slot in the housing.

9 Claims, 14 Drawing Sheets

LANCING DEVICE HAVING A RELEASABLE CONNECTOR

BACKGROUND OF THE INVENTION

1. Field of the Invention

This invention relates to a lancing device to pierce the skin to obtain a blood sample; more particularly, a lancing device that has a shortened stroke for ejecting the lancet after lancing.

2. Background of the Related Art

Lancing devices are an unfortunate fact of life for the millions of people with diabetes who must test their blood glucose levels up to five or more times each day. They typically use the devices to draw a drop of blood from a finger, apply the blood to a disposable strip, and measure the blood glucose concentration in a meter. Obvious goals of such lancing devices are to provide an adequate sample of blood with minimal pain, inconvenience, and cost to the user.

U.S. Pat. No. 4,503,856, issued on Mar. 12, 1985 to Cornell et al., discloses a lancet device that has a tubular housing, a slidable lancet holder in the housing and a compressible spring that provides the force to move the holder linearly to a skin piercing position, after which it goes back to a neutral position.

U.S. Pat. No. 4,527,561, issued on Jul. 9, 1985 to Burns, discloses a lancet assembly that includes a second spring for retracting the lancet holder after the lancet has penetrated the user's skin (see also U.S. Pat. Nos. 4,535,769 and 4,553,541).

U.S. Pat. No. 4,895,147, issued on Jan. 23, 1990 to Bodicky et al., discloses a lancet device that includes a penetration depth selector and a mechanism for creating a vacuum after the skin has been pierced to assist in drawing blood from the puncture site.

U.S. Pat. No. 4,976,724, issued on Dec. 11, 1990 to Nieto et al., discloses a lancet device that includes a mechanism that permits the user to eject a used lancet without touching it.

U.S. Pat. No. 5,318,584, issued on Jun. 7, 1994 to Lange et al., discloses a lancet device that includes a rotary/sliding transmission system that permits a puncture to be made with less pain.

SUMMARY OF THE INVENTION

The present invention provides a lancing device for withdrawing a blood sample. It comprises a generally elongate housing having a cap with a through hole at a forward end and a closure at a back end, opposite the forward end, and containing (a) a lancet holder, slidably mounted within the housing,
(b) a first spring for urging the holder forward, having a first end that bears on the housing and a second end that bears on the holder,
(c) a slider, slidably mounted in a wall of the housing, comprising
  (i) a projection outside the wall and
  (ii) a pushing means, reversibly engageable with the holder, to push the holder back into a cocked position and to push a lancet forward from the device,
(d) a second spring for urging the holder back, having a first end that bears on the holder and a second end that bears on the slider,
(e) a button, movable between a first position in which the holder is restrained when the device is cocked and a second position in which the restraint is removed, permitting the first spring to thrust the holder forward, and
(f) a releasable connector mounted within the housing for immobilizing the holder when the slider is moved forward to eject the lancet from the device.

Several advantages result from the releasable connector of the present lancing device. First, it permits the cocking and ejecting mechanisms not to be directly linked, permitting a shortened stroke. A shorter stroke facilitates one-handed operation of the device. In addition, a shorter stroke permits a shorter slot for the slider travel. By using a shorter slot, it is possible to provide the slot with a covering to prevent infiltration of debris, without the covering interfering with the actuator during ejection of the lancet.

Another advantage of the releasable connector is that it creates interference between the slider and the housing during lancet ejection, which provides friction feedback to let the user know that the device is in the ejection mode. The interference also eliminates the need for a return spring to provide tension for the slider. If there were no interference, the slider would be (undesirably) free to move around.

Still another advantage of the releasable connector is to prevent the slider from moving forward unintentionally when the cap is removed. Instead, the slider is forced forward against a stop on the connector by the second (retraction) spring. The connector thereby permits the cap to be removed and refastened without interference from the slider.

DETAILED DESCRIPTION OF THE INVENTION

The present invention provides a lancing device that incorporates a releasable connector for simpler construction and more convenient operation.

Figure 1:
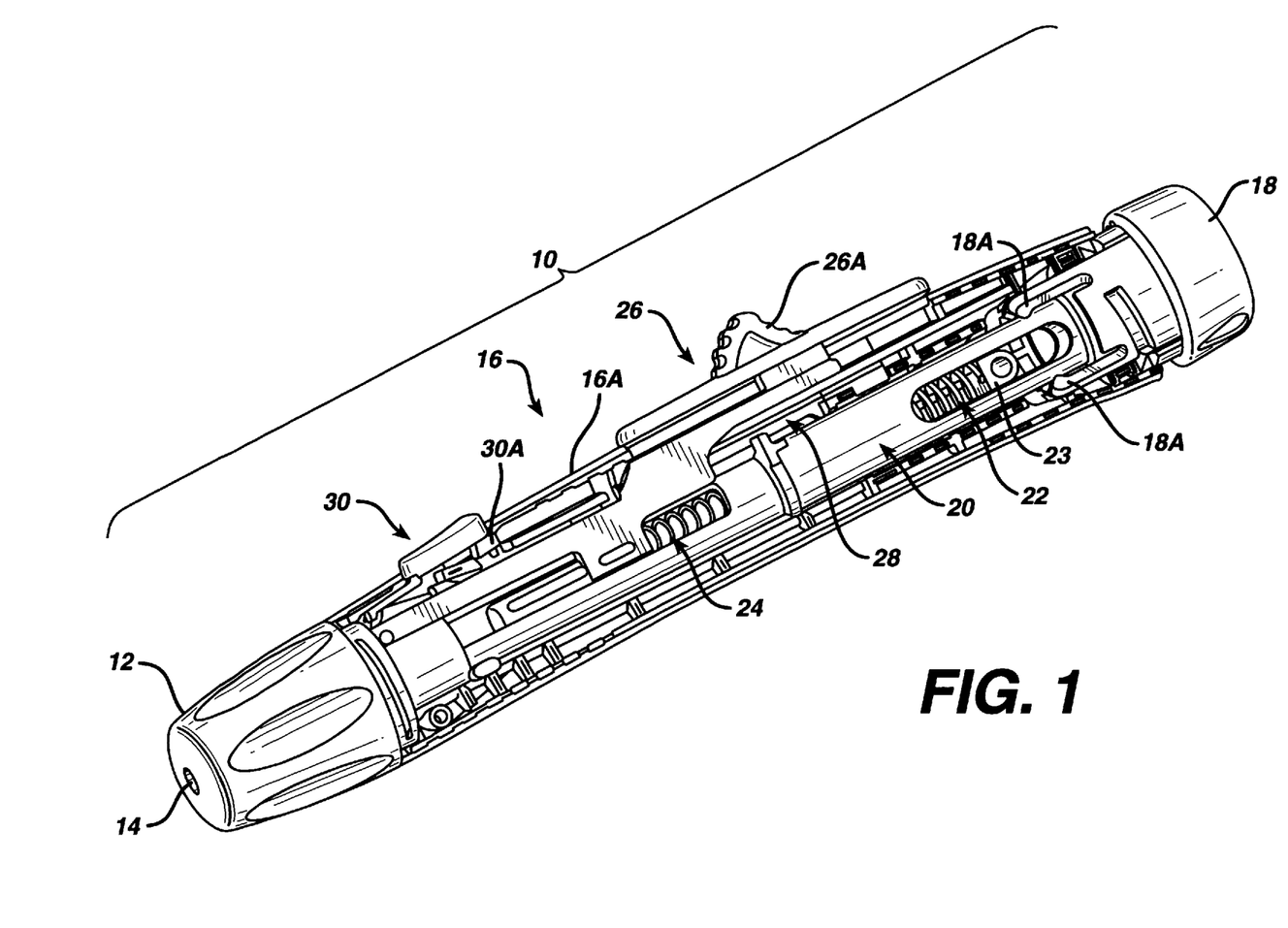
FIG. 1 is a perspective view of a device of this invention with half the housing removed.

FIG. 1 depicts a lancing device 10 of this invention, with one side of the housing removed to permit a view of the interior. The front end of the device has cap 12, with through hole 14. Cap 12 is removably joined, for example by a screw thread, to the housing 16, which is conveniently of two parts. One half 16A is shown, while the other half has been removed. At the back end of the device opposite cap 12, housing 16 is joined to knob 18. Knob 18 has cantilever fingers 18A that provide a mechanical stop, whose position can be varied by a thread, such as a helical thread, that attaches the knob to the housing. The mechanical stop is preferably provided by undercuts on the inside of the cantilever fingers.

A lancet holder 20 holds and guides a disposable lancet throughout the operation of the device. A drive spring 22 stores the energy needed for driving the lancet forward. Drive spring 22 is contained within holder 20 and bears on post 23 of the housing. A second, "retraction" spring 24, also contained in holder 20, provides a mechanism for removing the lancet needle from the skin after the skin has been punctured. The spring constant of retraction spring 24 is substantially less than that of drive spring 22; thus, drive spring 22 is substantially "stronger." Slider 26 is slidably mounted on housing 16 and has a projection 26A outside the housing that is manually movable—back to cock the device and forward to eject the lancet. When the device is being cocked, slider 26 engages holder 20. Button 30 is mounted through the housing, with tab 30A projecting inside the housing. After the device is cocked, pushing button 30 releases the restraint on lancet holder 20 to permit spring 22 to thrust the holder forward. Reference to element 30 as a "button" is not to suggest that the actuator element pictured is the only one contemplated. As used in this specification and the appended claims, "button" is to be understood as applying broadly to any actuator, of the type well known in the art, that can release the restraint on the lancet holder.

The operation of the lancing device can be understood with the help of a series of Figs. that show the configuration of the elements of the device in sequence during device operation.

Figure 2:
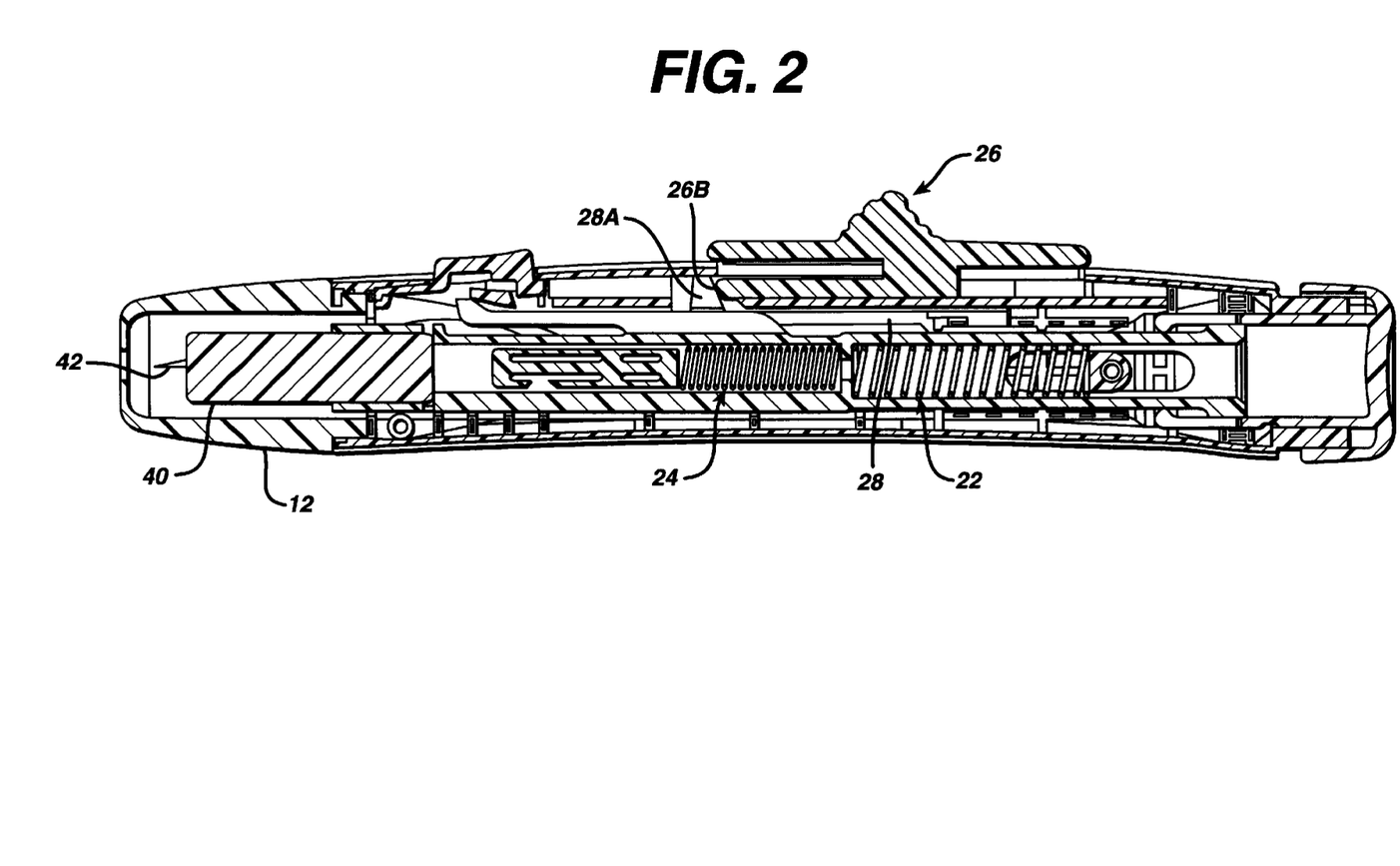
FIG. 2 is a cross section of the device of FIG. 1 in its rest position.

FIG. 2 shows a cross section of the device at rest, with the internal part 26B of slider 26 resting against top 28A of releasable connector 28. Drive spring 22 and retraction spring 24 are in balance, bearing on one another. Both springs are compressed, drive spring 22 much less than return spring 24, because its spring constant is much larger. Lancet 40 and needle 42 are seen inside cap 12.

Figure 3:
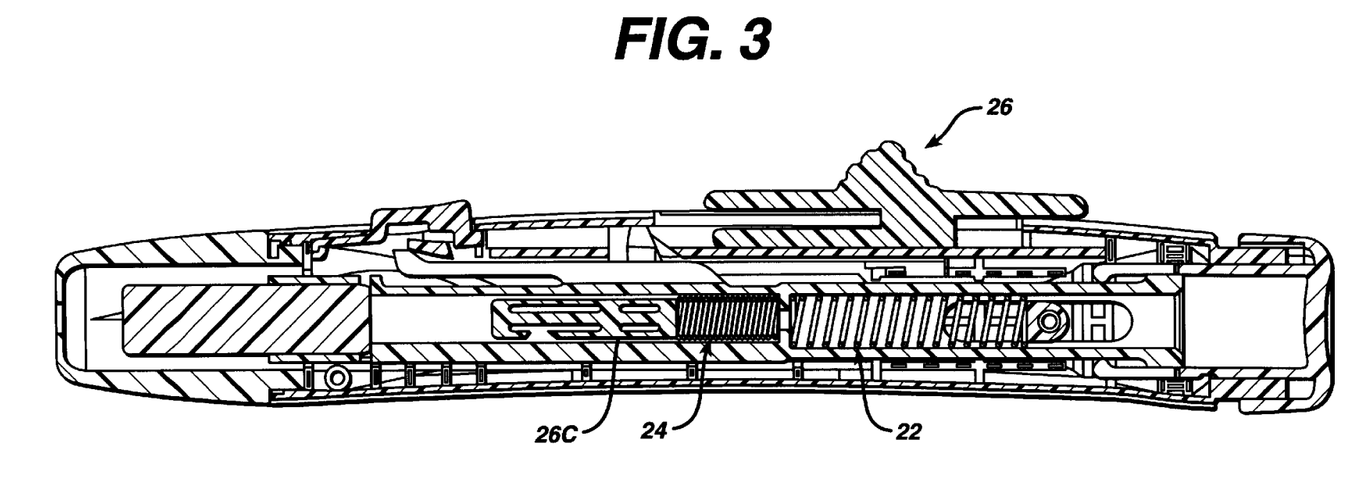
FIG. 3 is a cross section of the device of FIG. 1 as it is being cocked.

FIG. 3 shows a cross section of the device in an intermediate position as it is in the process of being cocked, by slider 26 being moved back (to the right in FIG. 3). The force exerted by the backward motion of pushing element 26C of slider 26 causes retraction spring 24 to be compressed more than in FIG. 2. Because of its much larger spring constant, drive spring 22 remains relatively uncompressed.

Figure 4:
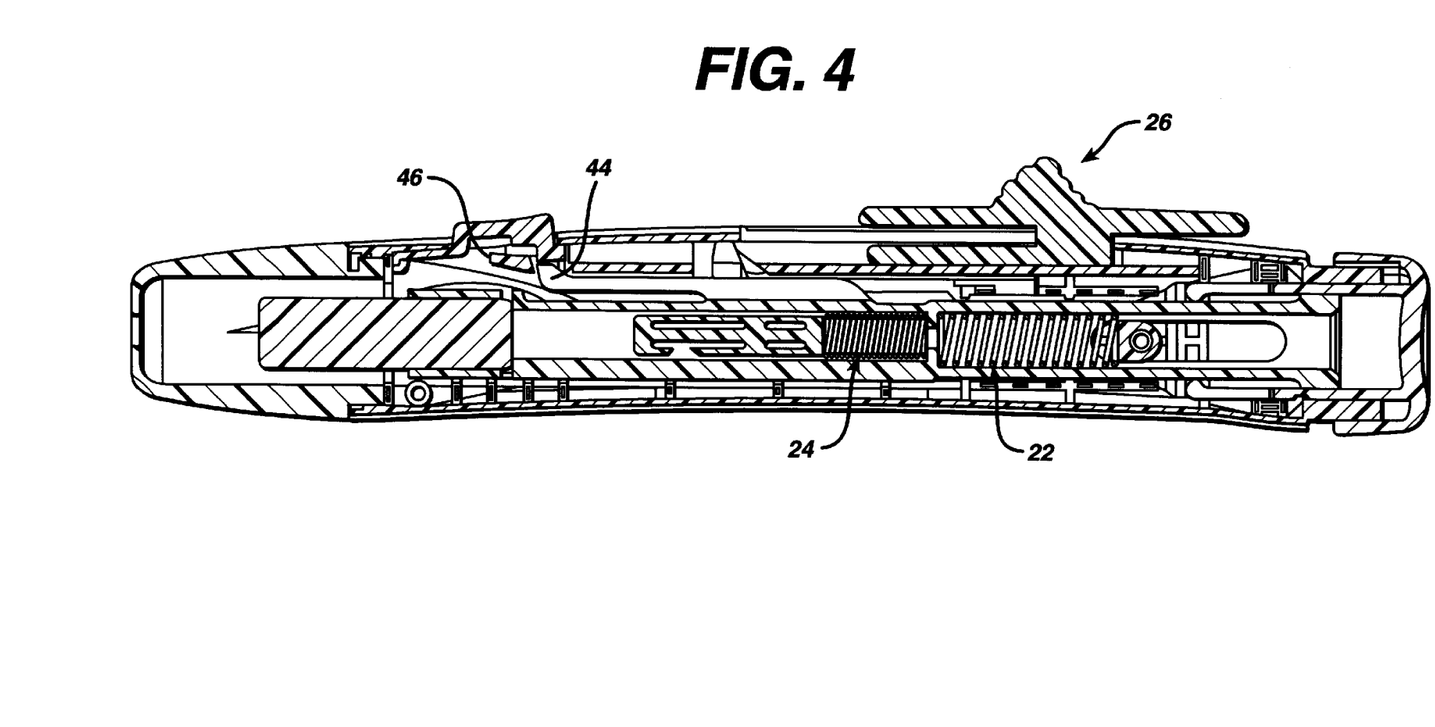
FIG. 4 is a cross section of the device of FIG. 1 in the over-cocked position.

FIG. 4 depicts the lancing device when it is in the "over-cocked" position; i.e., slider 26 has been moved to the far rearward position of its travel. Cantilever extension 44 of lancet holder 20 has moved slightly beyond (to the right of) housing stop 46. Drive spring 22 is compressed and retraction spring 24 remains compressed to about the same degree as in FIG. 3.

Figure 5:
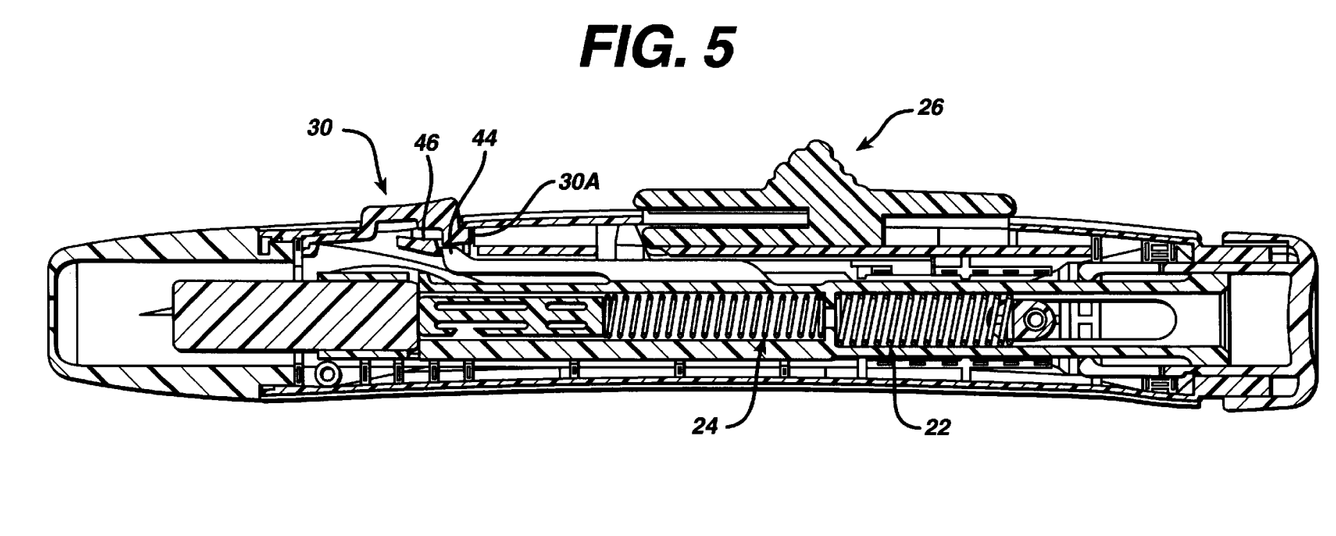
FIG. 5 is a cross section of the device of FIG. 1 when it is cocked.

FIG. 5 depicts the lancing device when it is cocked and at rest. Drive spring 22 is forcing extension 44 of lancet holder 20 against housing stop 46. Slider 26 has returned to its initial (FIG. 2) position. Retraction spring 24 is less compressed than in FIGS. 3 and 4. If button 30 is now pushed, tab 30A pushes extension 44 free of (under) stop 46 and enables lancet holder 20 to be thrust forward (to the left) in response to the force exerted by compressed drive spring 22.

Figure 6:
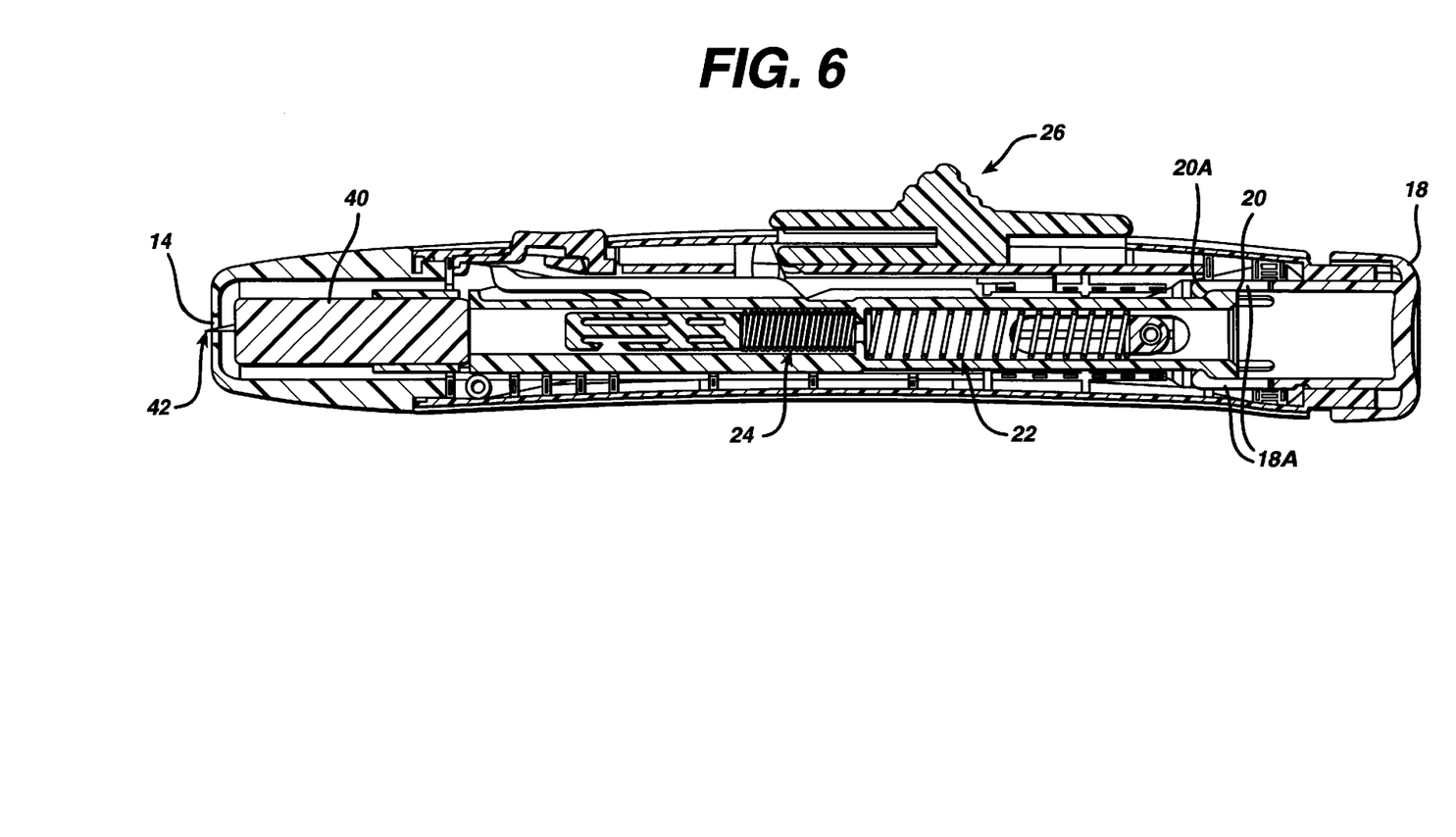
FIG. 6 is a cross section of the device of FIG. 1 as it is being fired.

That sequence leads to the instantaneous situation depicted in FIG. 6, in which lancet 40 has reached its extreme left position, with needle 42 protruding through cap opening 14. Lancet holder 20 has been stopped in its forward (leftward) motion by protuberances on cantilever fingers 18A, which are internal elements of knob 18. As was discussed earlier, the cantilever fingers deflect slightly, whereby they absorb some vibration and reduce noise to reduce pain to the user. Slider 26 is still at its initial position. Drive spring 22 has been thrown forward with holder 20 and is uncompressed. Retraction spring 24 is compressed, whereby it will exert a force rearward (to the right) on holder 20, with the result that lancet 40 and needle 42 will be retracted and the configuration of the elements will return to that shown in FIG. 2.

Figure 7:
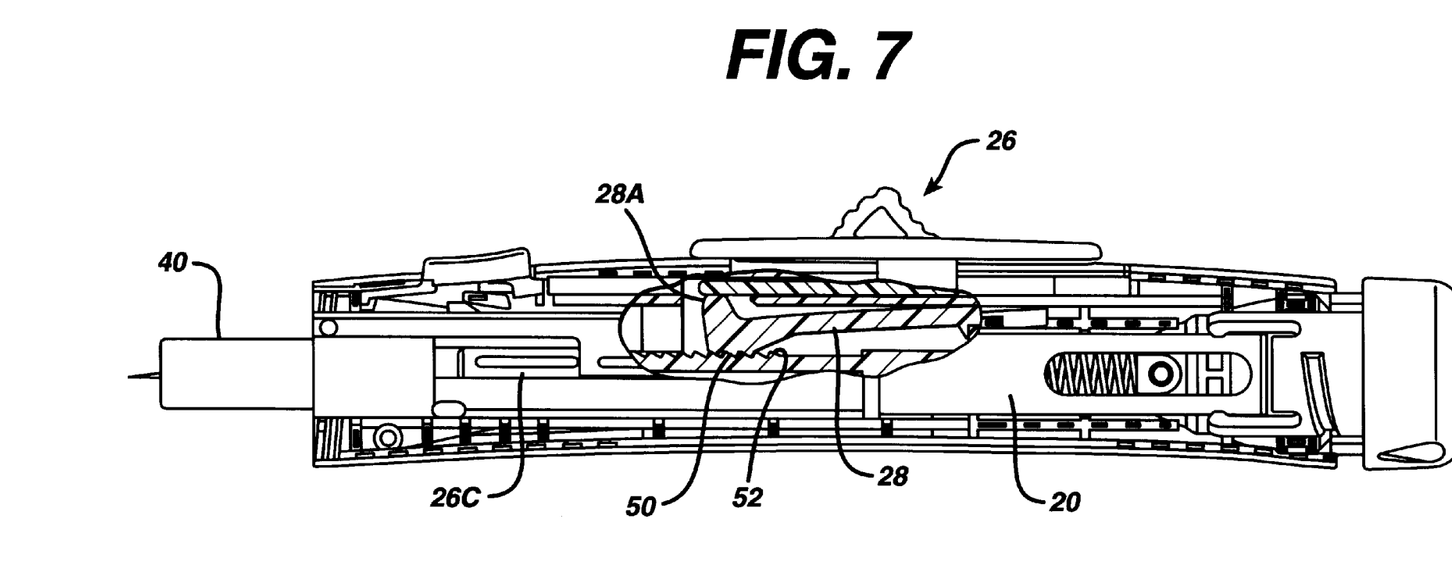
FIG. 7 is a cross section that depicts lancet ejection from a device of this invention.

Following a piercing operation, the used lancet must be removed from the device. FIG. 7 is a section in partial cutaway that depicts the lancet ejection when the releasable connector 28 is a cantilever latch. Cap 12 must first be removed. As slider 26 is moved forward, it pushes down the top 28A of latch 28, forcing teeth 50 on latch 28 to mesh with corresponding teeth 52 on holder 20, preventing the holder from moving forward, as the pushing element 26C of slider 26 pushes the used lancet 40 out of the device. By locking the holder in place during the process, a desirably shorter slider stroke serves to accomplish the ejection. In addition, friction between the slider and top 28A provides desirable tactile feedback to a user during the ejection step.

Figure 7A:
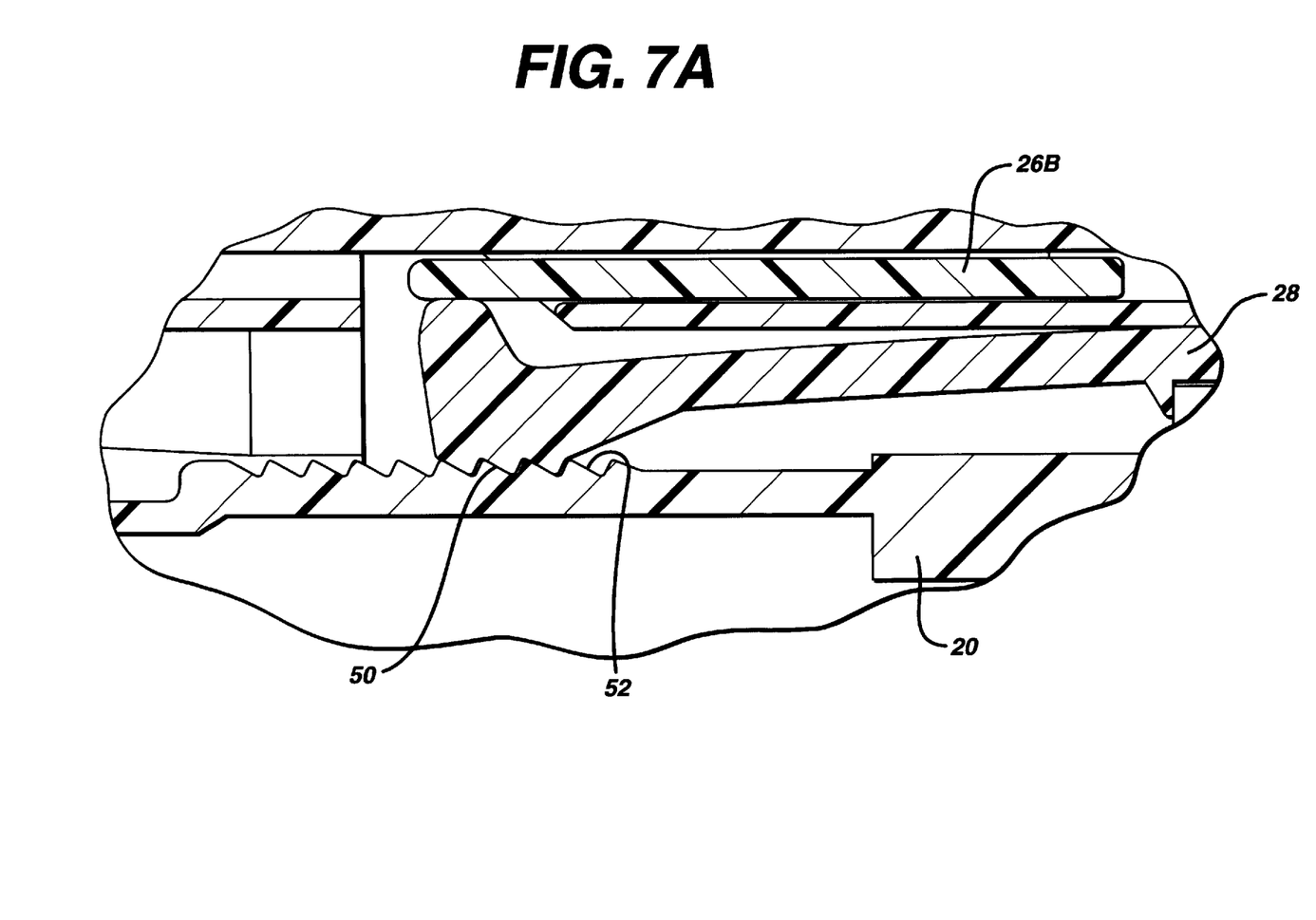
FIGS. 7A–7F are enlarged views of a part of FIG. 7, showing various alternative embodiments of a releasable connector.

FIG. 7A focuses on the construction of the cantilever latch 28 and its teeth 50 that engage corresponding teeth 52 on holder 20. As shown, both sets of teeth are asymmetrical, which is preferred for the following reason. Although the device is preferably cocked by moving slider 26 back, as discussed above in connection with FIGS. 3, 4, and 5, it can also be cocked by pushing a fresh lancet 40 into the device after a used lancet has been ejected. In that case, the cantilever latch and holder may still have their teeth engaged, as shown in FIG. 7A. But the asymmetric teeth will permit the holder to move back (to the right) to reach, sequentially, the positions shown in FIGS. 3, 4, and 5.

Figure 8:
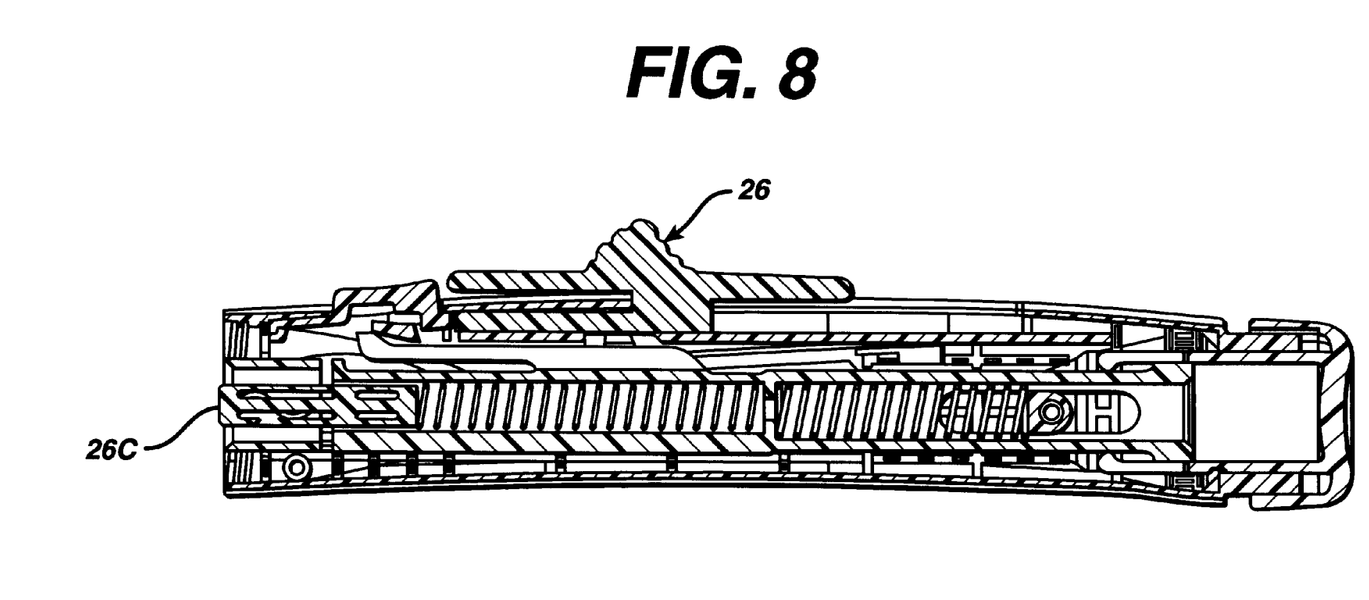
FIG. 8 is a cross section of a device of this invention after lancet ejection.

FIG. 8 shows the elements of the device when slider 26 has been pushed forward to the end of its travel, causing pushing element 26C of slider 26 to drive the lancet (not shown) from the device.

Although FIGS. 7 and 7A depict a preferred releasable connector 28, in which a cantilever latch has a cantilever arm for releasable contact with holder 20 and teeth 50 on the latch to engage teeth 52 on the holder, other embodiments of the releasable connector are also contemplated in this invention. These are depicted in a series of figs. that show focused views of the parts of the alternative releasable connectors that correspond to the parts of the cantilever latch shown in FIG. 7A.

Figure 7B:
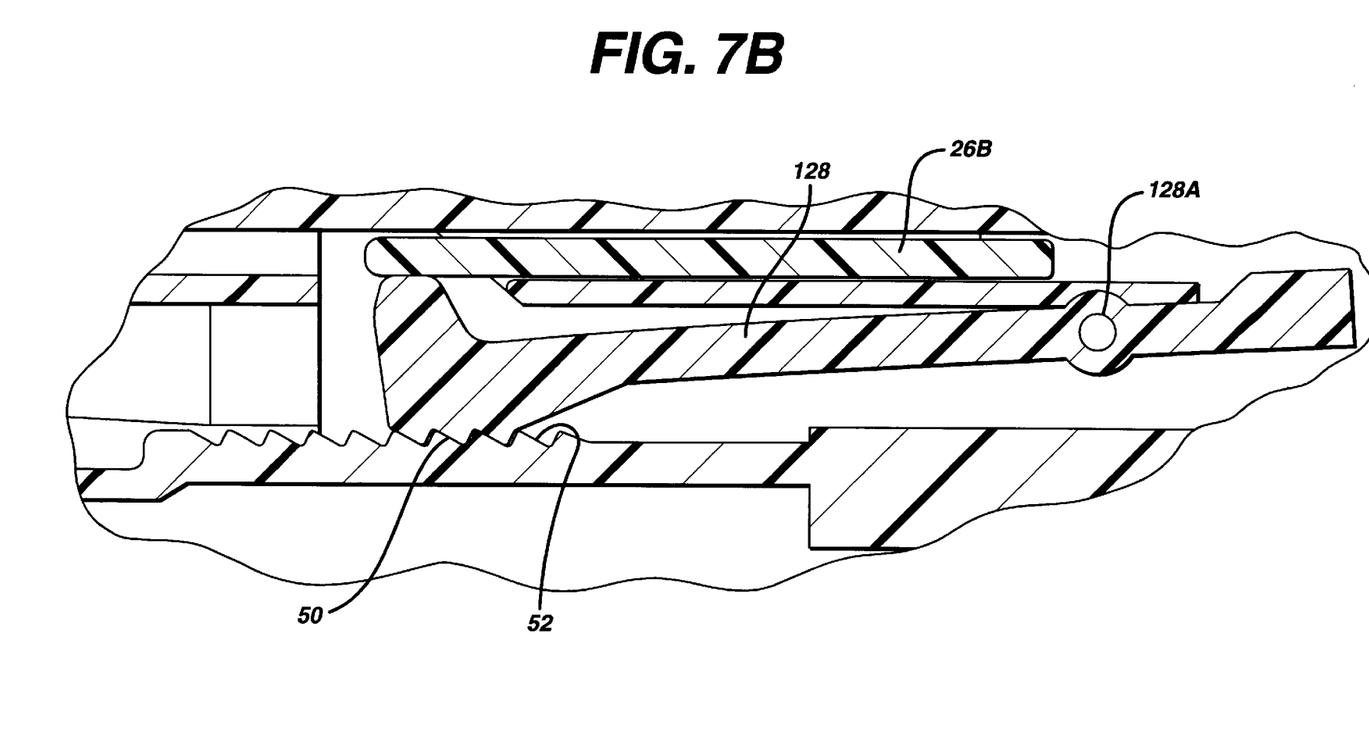

FIG. 7B depicts a connector in which the arm 128 has a pivot 128A rather than being cantilevered.

Figure 7C:
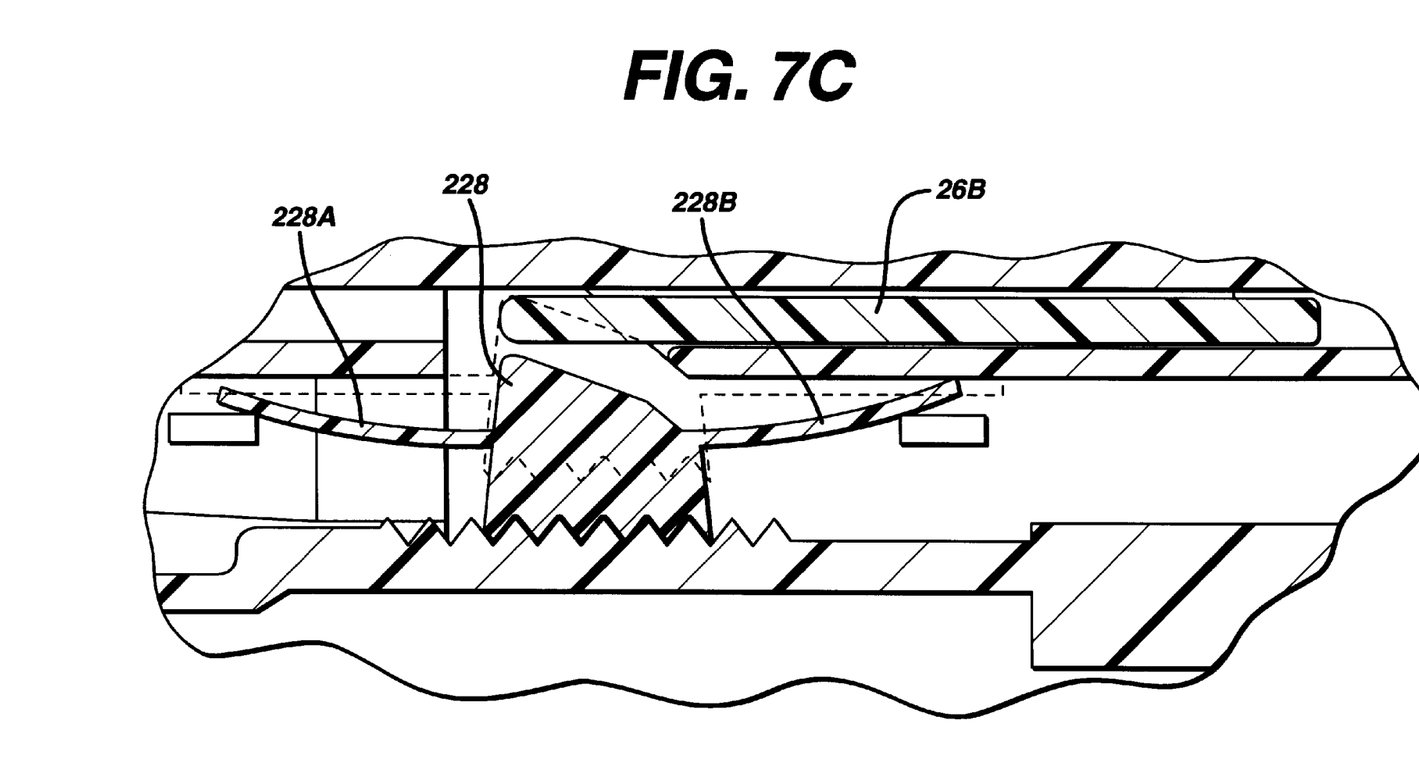

FIG. 7C depicts a connector in which arm 228 is spring-loaded, supported by leaf springs 228A and 228B. Clearly other types of springs, such as coil springs, could be used. FIG. 7C illustrates the fact that the term "arm" is not to be interpreted as necessarily referring to an elongated element; rather, it simply identifies the element that carries the engaging mechanism.

Figure 7D:
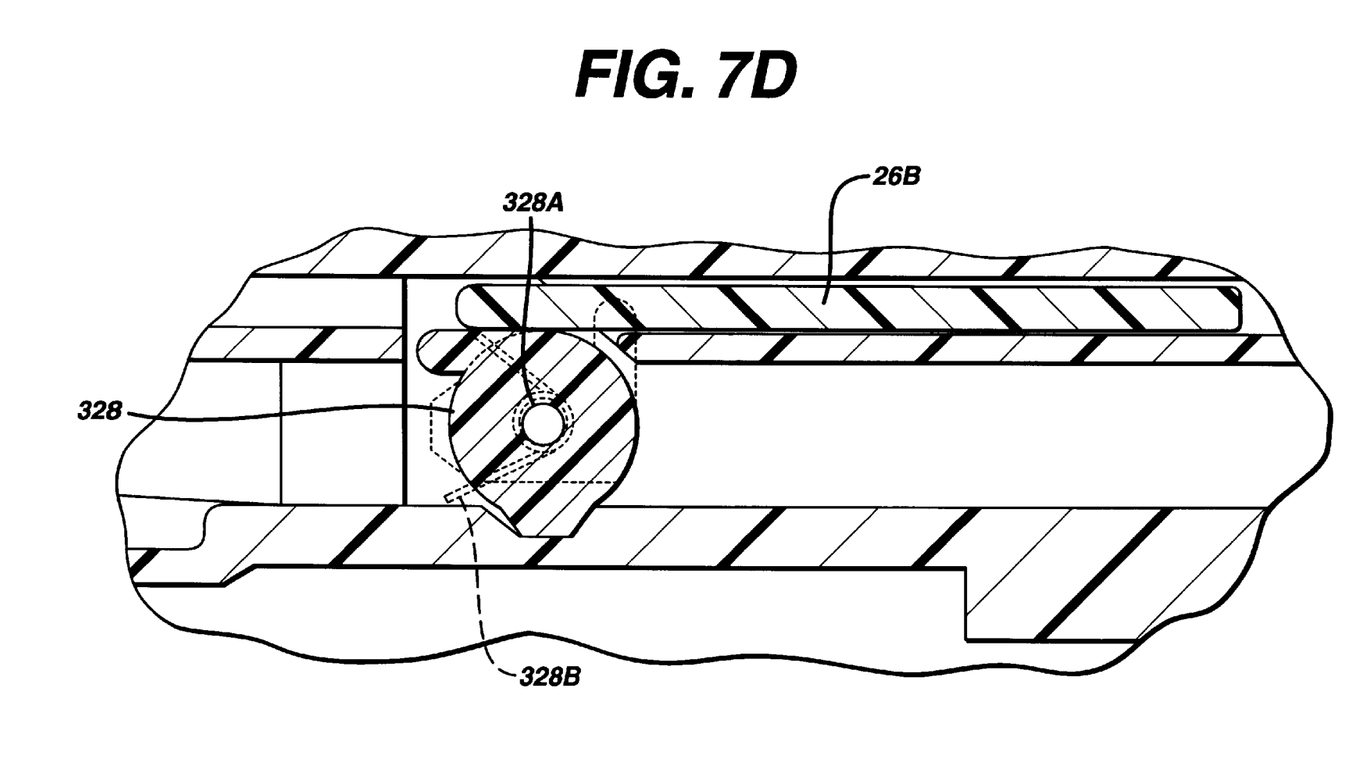

FIG. 7D depicts a connector in which arm 328 is rotatably mounted on axis 328A, spring-loaded with a torsion spring 328B.

Figure 7E:
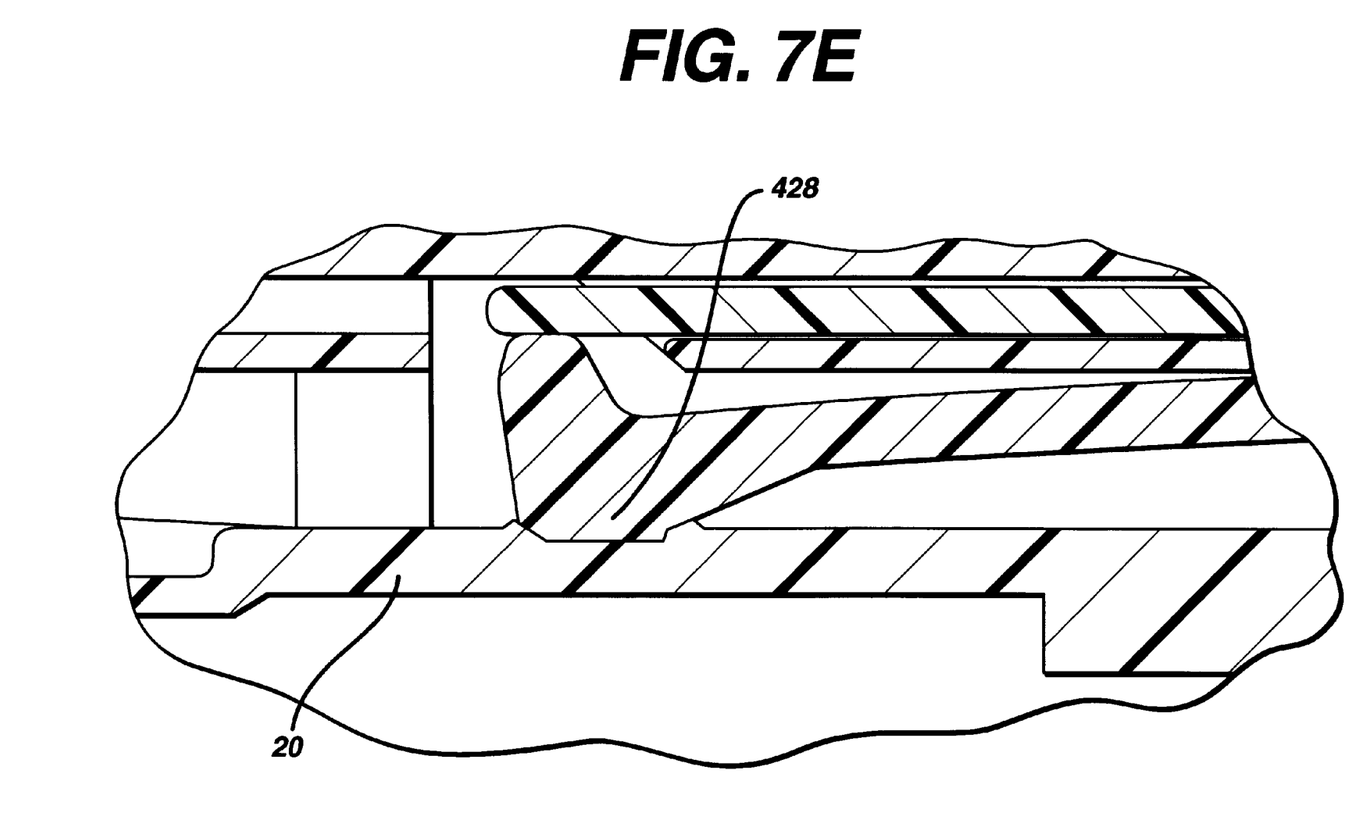

FIG. 7E depicts an embodiment in which holder 20 has a reversibly deformable surface that is deformed by connector 428 to immobilize the holder.

Figure 7F:
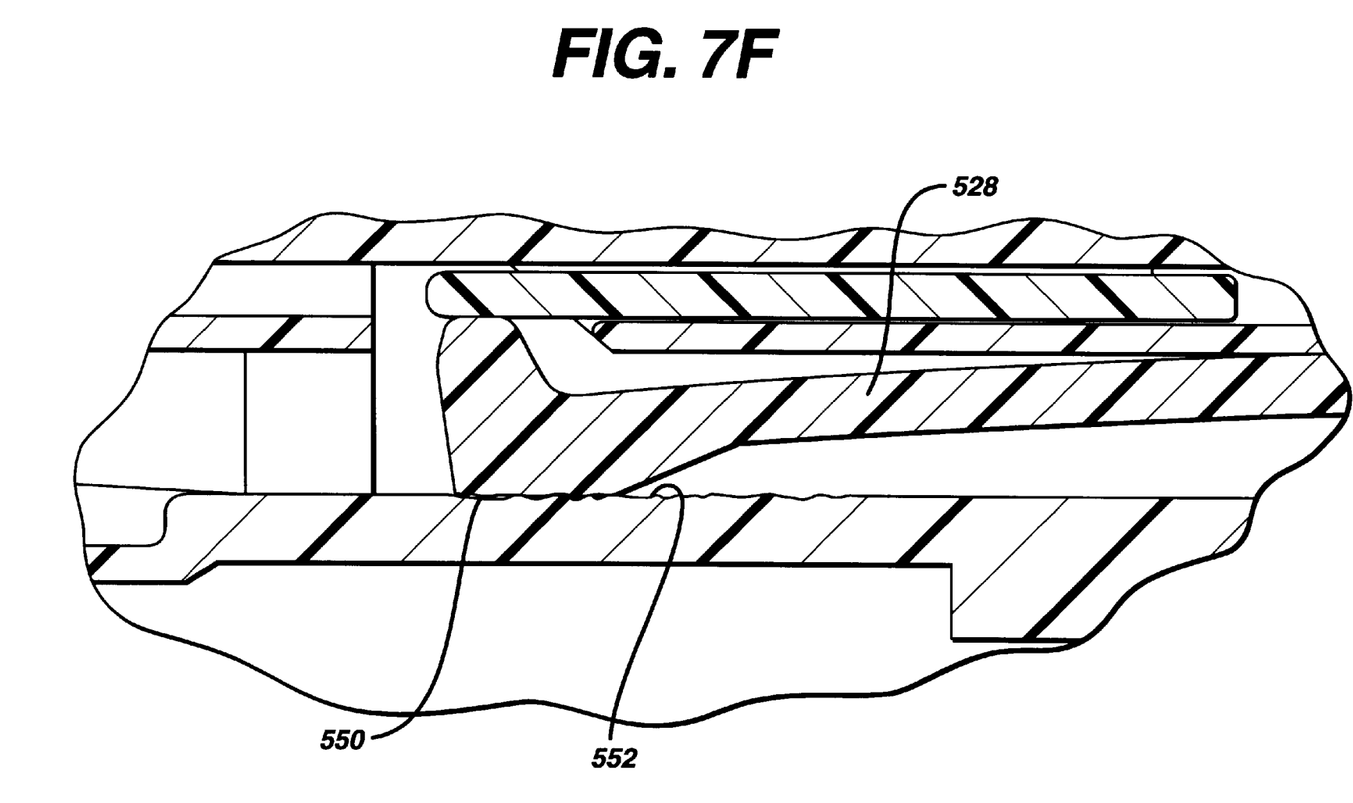

FIG. 7F depicts an embodiment in which cantilever connector 528 has a rough surface 550 that engages a rough surface 552 on the holder to immobilize the holder.

It will be understood by those skilled in the art that the foregoing description and figures are illustrative of practicing the present invention, but are in no way limiting. Variations of the detail presented herein may be made without departing from the scope and spirit of the present invention.

We claim:

1. A lancing device for withdrawing a blood sample, comprising a generally elongate housing having a cap with a through hole at a forward end and a closure at a back end, opposite the forward end, and containing
   (a) a lancet holder, slidably mounted within the housing,
   (b) a first spring for urging the lancet holder forward, having a first end that bears on the housing and a second end that bears on the lancet holder,
   (c) a slider, slidably mounted in a wall of the housing, comprising
      (i) a projection outside the wall and
      (ii) a pushing means, reversibly engageable with the lancet holder, to push the lancet holder back into a cocked position and to push a lancet forward from the device,
   (d) a second spring for urging the lancet holder back, having a first end that bears on the lancet holder and a second end that bears on the slider,
   (e) a button, movable between a first position in which the lancet holder is restrained when the device is cocked and a second position in which the restraint is removed, permitting the first spring to thrust the lancet holder forward, and
   (f) a releasable connector mounted within the housing for immobilizing the lancet holder when the slider is moved forward to eject the lancet from the device.

2. The device of claim 1, further comprising a lancet mounted in the lancet holder, the lancet including a needle having a point for passing through the hole in the cap to effect a piercing operation.

3. The device of claim 1 in which the releasable connector comprises a cantilever arm.

4. The device of claim 1 in which the releasable connector comprises a pivoted arm.

5. The device of claim 1 in which the releasable connector comprises a spring-loaded arm.

6. The device of claim 1 in which the releasable connector has a rough surface near a forward end for frictionally engaging a rough surface on the lancet holder.

7. The device of claim 1 in which the releasable connector has at least one tooth near a forward end for engaging at least one depression in the lancet holder.

8. The device of claim 7 in which the releasable connector has a plurality of asymmetric teeth for engaging a plurality of asymmetric teeth on the lancet holder.

9. The device of claim 1 in which the lancet holder has a reversibly deformable surface that is deformed by the releasable connector to reversibly immobilize the lancet holder.

\* \* \* \* \*